US008110211B2

(12) United States Patent
Pacetti et al.

(10) Patent No.: US 8,110,211 B2
(45) Date of Patent: Feb. 7, 2012

(54) MEDICATED COATINGS FOR IMPLANTABLE MEDICAL DEVICES INCLUDING POLYACRYLATES

(75) Inventors: Stephen Dirk Pacetti, San Jose, CA (US); Thierry Glauser, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2074 days.

(21) Appl. No.: 10/948,036

(22) Filed: Sep. 22, 2004

(65) Prior Publication Data
US 2006/0062824 A1 Mar. 23, 2006

(51) Int. Cl.
A61F 2/00 (2006.01)
A61F 2/06 (2006.01)
C08F 118/02 (2006.01)
(52) U.S. Cl. .................. 424/423; 526/319; 623/1.42
(58) Field of Classification Search ............... None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |

(Continued)

FOREIGN PATENT DOCUMENTS
DE 42 24 401 1/1994
(Continued)

OTHER PUBLICATIONS

Yoshikawa et al. Colloid and Polymer Science 1978 256:422-426.*
Rubin The Elements of Polymer Science and Engineering. San Diego: Academic Press, 1999 p. 28-33.*
International Search Report for PCT/US2005/032754, filed Sep. 12, 2005, mailed Jun. 22, 2006, 13 pgs.
U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.
U.S. Appl. No. 10/251,111, filed Sep. 19, 2002, Hossainy et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.

Primary Examiner — Robert A Wax
Assistant Examiner — Caralynne Helm
(74) Attorney, Agent, or Firm — Squire Sanders (US) LLP

(57) ABSTRACT

A polymer for a medical device, particularly for a drug eluting stent, is described. The polymer can be derived from n-butyl methacrylate and can have a degree of an elongation at failure from about 20% to about 500%.

17 Claims, No Drawings

U.S. PATENT DOCUMENTS

| | | | |
|---|---|---|---|
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,834,408 A * | 11/1998 | Mishra et al. | 508/469 |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,096 A * | 9/1999 | Santos et al. | 424/434 |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,616,765 B1 | 9/2003 | Hossaony et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,703,466 B1 | 3/2004 | Karakelle et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |

| Publication No. | Date | Inventor | Class |
|---|---|---|---|
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0026236 A1* | 2/2002 | Helmus et al. | 623/1.42 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0199964 A1* | 10/2003 | Shalaby et al. | 623/1.11 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |
| 2006/0280771 A1* | 12/2006 | Groenewegen et al. | 424/426 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/000383 | 12/2003 |
| WO | WO 04/009145 | 1/2004 |
| WO | WO 2004/009145 | 1/2004 |
| WO | WO 2005/053937 | 6/2005 |
| WO | WO 2005/081878 | 9/2005 |
| WO | WO 2006/031532 | 3/2006 |

* cited by examiner

MEDICATED COATINGS FOR IMPLANTABLE MEDICAL DEVICES INCLUDING POLYACRYLATES

BACKGROUND

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to re-duce the chance of the development of thrombosis and restenosis, a stent is implanted in the lumen to maintain vascular patency.

Stents are used not only as a mechanical intervention but also as a vehicle for providing biological therapy. As a mechanical intervention, stents act as scaffoldings, functioning to physically hold open and, if desired, to expand the passageway. Typically, stents are capable of being compressed, so that they can be inserted through small vessels using catheters, and then expanded to a larger diameter once they are at the desired location. Examples in the patent literature disclosing stents that have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Pharmacological therapy can be achieved by medicating the stents. Medicated stents provide for the local administration of a therapeutic substance at the diseased site. In order to provide an effective concentration at the treated site, systemic administration of such medication often produces adverse or toxic side effects for the patient. Local delivery is a preferred treatment method in that smaller total medication levels are administered compared to systemic dosages, but are concentrated at a specific site. Local delivery thus produces fewer side effects and achieves better results. One proposed method for medicating stents involves using a polymeric carrier coated onto the stent's surface. A solution, which includes a solvent, a polymer dissolved in the solvent, and a therapeutic substance dispersed in the blend is applied to the stent. The solvent is allowed to evaporate, leaving a coating of the polymer and the therapeutic substance impregnated in the polymer on the stent surface.

One polymer that can be used for making stent coatings is poly(n-butyl methacrylate) (PBMA). This polymer is durable, and biologically compatible, and can be used either as a polymeric matrix carrying the drug, or as a topcoat membrane regulating the release rate of the drug. However, PBMA has properties that can be improved. In particular, the release rate of some hydrophobic, medium-molecular-weight drugs, such as EVEROLIMUS, from the PBMA-based stent coatings can be too low. As a result, a higher drug-to-polymer ratio may be required, which is undesirable. At high drug-to-polymer ratios, some of the PBMA-based drug and polymer compositions can have insufficient elongation at high strains that expansion of the stent creates in the coating.

The embodiments of the invention provide stent coatings that are free of the above-described deficiencies and possess other beneficial properties.

SUMMARY

Various embodiments encompass medical articles comprising a polymer derived from a base polymer comprising residues of a base monomer (which when polymerized yields the base polymer), wherein the base polymer has a degree of elongation at failure of from 20-500%. In some of these embodiments, the polymer comprises a base polymer with a weight-average molecular weight of about 200 k-1000 k Daltons. In these or other embodiments, the base polymer has a polydispersity index of about 3 to about 6. In these or other embodiments, the polymer has a glass transition temperature of below about 20° C.; alternatively from −30 to 20° C.

In these or other embodiments, the polymer includes at least a first acrylic monomer. Some embodiments select the polymer to be a mixture of at least a first acrylic monomer and the base polymer; some select the polymer to be a copolymer of base monomers and first acrylic monomers.

In these or other embodiments, the first acrylic monomer is at least one of n-hexyl methacrylate, 2-ethylhexyl methacrylate, lauryl methacrylate (dodecyl methacrylate), n-octyl methacrylate, n-heptyl methacrylate, n-nonyl methacrylate, 2-ethoxyethyl methacrylate, 2-methoxyethyl methacrylate, pentyl methacrylate, iso-decyl methacrylate, n-decyl methacrylate, n-dodecyl methacrylate), 1-hexadecyl methacrylate, undecyl methacrylate, 3,5,5-trimethylhexyl methacrylate or an combination of these monomers. In some embodiments, the first acrylic monomer is chosen from a group that specifically excludes any one or any combination of these monomers.

In some embodiments, the polymer has one of the following formulas:

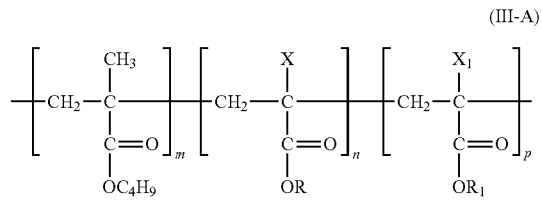

(III-A)

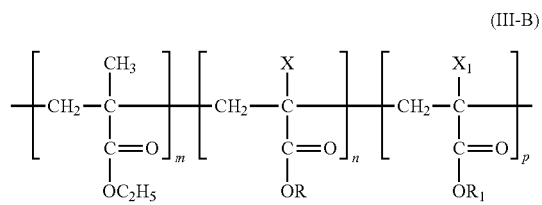

(III-B)

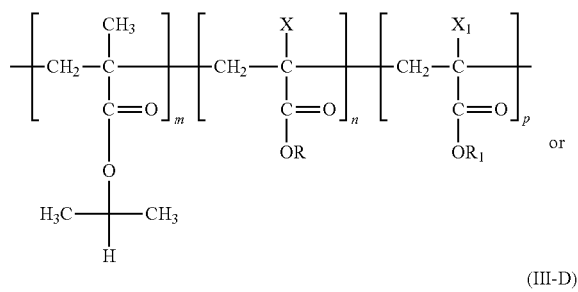

(III-C)

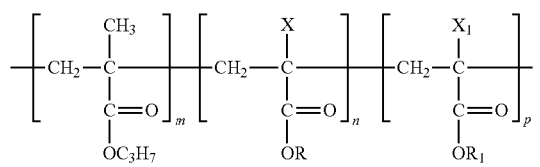

(III-D)

wherein X and $X_1$ are each, independently, a hydrogen atom or an alkyl group, R and $R_1$ are each, independently, a $C_1$-to-$C_{12}$ straight-chained or branched aliphatic radical, and m, n, and p are each integers in which m>0, n>0, and p≧0.

In these or other embodiments, the base polymer comprises at least one of or any combination of poly(n-butyl methacrylate), poly(ethyl methacrylate), poly(isopropyl methacrylate), or poly(n-propyl methacrylate). In some embodiments, the base polymer is chosen from a group that specifically excludes any one or any combination of these.

In these or other embodiments, the polymer comprises poly(n-butyl methacrylate) and a second polymeric material wherein the polymer has a substantially single, glass transition temperature. In some of these embodiments, that substantially single, glass transition temperature is below about 20° C.; alternatively from −30° C. to about 20° C.

In these or other embodiments, the second polymeric material is at least one of poly(n-hexyl methacrylate), poly(n-heptyl methacrylate), poly(2-ethylhexyl methacrylate), poly(n-octyl methacrylate), poly(n-nonyl methacrylate), poly(2-ethoxyethyl methacrylate), poly(2-methoxyethyl methacrylate), poly(pentyl methacrylate), poly(iso-decyl methacrylate), poly(n-decyl methacrylate), poly(1-hexadecyl methacrylate), poly(undecyl methacrylate), poly(3,5,5-trimethylhexyl methacrylate, poly(lauryl methacrylate), or an combination of these. In some embodiments, the second acrylic monomer is chosen from a group that specifically excludes any one or any combination of these monomers.

In these or other embodiments, the second polymeric material comprises a non-acrylic polymer with a Tg below that of the base polymer.

In these or other embodiments, the medical device additionally comprises one or any combination of these agents: vascular-smooth-muscle-cell-activity inhibitors, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, or salts of these. In some embodiments, the agents are chosen from a group that specifically excludes any one or any combination of these categories.

Methods of making the embodiments discussed above are also within the scope of this invention.

In some invention embodiments, the implantable medical device is a stent.

DETAILED DESCRIPTION

Terms and Definitions.

The following terminologies and definitions apply:

The term "polymer" is defined to be inclusive of homopolymers, copolymers, and terpolymers. The term "polymer" is further defined as a synonym of the term "polymeric compound". The term "copolymer" is defined as a polymer derived from more than one species of monomer, including copolymers that are obtained by copolymerization of two monomer species and those obtained from three monomers species ("terpolymers"). The term "random co-polymer" is defined as a copolymer consisting of macromolecules in which the probability of finding a given monomeric unit at any given site in the chain is independent of the nature of the adjacent units. The term "alternating copolymer" is defined as a copolymer consisting of macromolecules comprising two species of monomeric units in alternating sequence.

The term "polydispersity", expressed as the polydispersity index (PI), refers to the molecular weight distribution of a polymer, since every polymer comprises molecules having a variety of chain lengths and thus a variety of molecular weights. The term "polydispersity index" is defined as the ratio $M_w/M_n$ of the weight-average molecular weight of a polymer ($M_w$) to the number-average molecular weight of the same polymer ($M_n$).

The term "weight-average molecular weight" ($M_w$) is defined as the molecular weight of a polydisperse polymer sample, averaged to give higher statistical weight to larger molecules; calculated as $$M_w = \Sigma(M_i^2 N_i)/(M_i N_i),$$

where $M_i$ is a molecular weight of a macromolecule of a fraction "i", and $N_i$ is a number of macromolecules in the "i" fraction.

The term "number-average molecular weight" ($M_n$) is defined as the molecular weight of a polydisperse polymer sample, averaged to give equal statistical weight to each molecule, calculated as $$M_n = \Sigma(M_i N_i)/\Sigma(N_i),$$

where $M_i$ and $N_i$ are as defined above.

For most polymers, it is a frequent phenomenon that $M_w > M_n$, and consequently PI>1.0. As the polymer's molecular weight distribution becomes narrower, the PI value approaches 1.0, and vice versa. For a theoretically monodisperse polymer, $M_w = M_n$; and for such polymer PI=1.0.

The term "glass transition temperature" or $T_g$ is defined as a temperature approximately in the middle of the temperature region where, as a result of exposure of an amorphous or semi-crystalline polymer to an increasing temperature, the onset of segmental molecular motion in the chains of the polymer occurs, leading to the eventual transition of the polymer from a glassy solid to an amorphous solid at atmospheric pressure. In other words, the $T_g$ is defined as an average temperature in the temperature region at which an amorphous polymer (or the amorphous regions in a partially crystalline polymer) changes from a hard and relatively brittle nature to a viscoelastic (rubbery) nature. For the purposes of the present invention, the $T_g$ for all polymers discussed below has been determined using differential scanning calorimetry (DSC) when the polymer is in a dry state. DSC measures the change in heat capacity of a polymer as a function of temperature. The "dry state" means that a polymer contains less than about 1% of water (as a percentage of the polymer's weight).

The term "acrylic polymers" or "acrylates" refers to polymers (inclusive of homopolymers, copolymers, terpolymers, oligomers, and prepolymers) derived from monomers having an acrylic group (I) or methacrylic group (II)

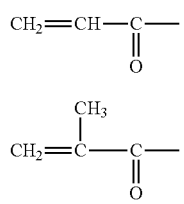

The term "maximum elongation" or "elongation at failure" is defined as the fractional increase in length of a free film of a polymer at the film rupture point, when the sample is stretched at a constant rate in a unidirectional, linear fashion.

EMBODIMENTS OF THE INVENTION

The stent coating can be a multi-layer structure that can include any one or any combination of the following layers:
 (a) a primer layer;
 (b) a drug-polymer layer (also referred to as "reservoir" or "reservoir layer") or alternatively a polymer-free drug layer;
 (c) a topcoat layer; or
 (d) a finishing topcoat.

In some embodiments, the multilayer structure may specifically exclude any one or any combination of the layers listed above.

Each layer of the stent coating can be formed on the stent by dissolving a polymer or a blend of polymers in a solvent or a solvent mixture, and applying the resulting solution to the stent by spraying or immersing it in the solution. After application the solvent evaporates leaving a dry coating. Drying can be accelerated by conducting it at an elevated temperature.

To incorporate a drug into the reservoir layer, the drug can be combined with the polymer solution described above. Alternatively, a polymer-free reservoir can be made. To fabricate a polymer free reservoir, the drug can be dissolved in a suitable solvent or solvent mixture, followed by applying the solution by spraying or immersing the stent in the drug solution.

Instead of introducing the drug as a solution, it can be introduced as a colloidal system, such as a suspension in an appropriate solvent. To make the suspension, the drug can be dispersed in the solvent using conventional colloid chemistry techniques. Depending on a variety of factors, e.g., the nature of the drug, those having ordinary skill in the art can select the solvent for the suspension, as well as the quantity of drug dispersed in the solvent. The suspension can be mixed with a polymer solution, and the mixture can be applied to the stent as described above. Alternatively, the drug suspension can be applied to the stent without being mixed with the polymer solution.

The drug-polymer layer can be applied directly to at least part of the stent surface to serve as a reservoir for at least one active agent or drug, which is incorporated into the reservoir layer. The optional primer layer can be applied between the stent and the reservoir to improve drug-polymer adhesion to the stent. The topcoat layer, if used, can be applied over at least a portion of the reservoir, and can serve as a rate limiting membrane, which helps to control drug release rate. In some embodiments, the topcoat layer can be essentially free of any active agents or drugs; nevertheless, during topcoat formation, a quantity of drug, however small, can migrate into the topcoat from the drug-polymer layer. The optional finishing layer can be applied to all or a part of the stent surface to enhance stent biocompatibility.

According to an embodiment of the present invention, any or all layer(s) of the stent coating can be a polymer derived from poly(n-butyl methacrylate) (PBMA), poly(ethyl methacrylate) (PEMA), poly(isopropyl methacrylate) (PIPMA), poly(n-propyl methacrylate) (PPMA) or copolymers including units derived from PBMA, PEMA, PIPMA, or PPMA having a high degree of an elongation at failure, such as from about 20% to about 500%, more narrowly, from about 30% to about 300%, for example, from about 40% to about 200%. For purposes of this disclosure, all of these polymers are referred to collectively as base polymers. Additionally, base-polymer unit means any monomeric unit from which a base polymer can be derived. Some invention embodiments specifically exclude any one or any combination of the polymers or base-polymer units listed above from inclusion as base polymers or base-polymer units.

According to embodiments of the present invention, various methods can be used to fabricate stent coatings that include base polymer or a base-polymer-unit-derived polymer with a high degree of elongation at failure. The following discussion describes these methods, which include:
 using a base polymer having high weight-averaged molecular weight ($M_w$);
 using a base polymer having a broad polydispersity index (PI); and
 using a base-polymer-unit-derived polymeric compositions having lower $T_g$ than that of base polymer.

Using a High-$M_w$ Base Polymer

According to an embodiment of the present invention, base polymers having high $M_w$ can be used. For example, useful base polymer $M_w$ can be about 100,000 Daltons to about 1,000,000 Daltons. Viscosity may be an issue at 1,000,000 MW, but adjusting the application of a viscous solution or adjusting the viscosity of a solution is within the skill level of ordinarily skilled artisans.

In some embodiments, base polymers can have $M_w$ from about 200,000 Daltons to about 600,000 Daltons, for example, from about 250,000 Daltons to about 500,000 Daltons.

Besides achieving higher degree of elongation at failure, using high molecular weight base polymers to make stent coatings is expected to improve many physical and mechanical properties of the coating. For example, tensile strength, yield strength, crack resistance, and abrasion resistance are all expected to improve.

Using Broad-PI Base Polymers

In some embodiments, in order to have base polymer with a high degree of elongation at failure, base polymer with a broad molecular weight distribution are used. For example, base polymer having a PI from about 3 to about 6 can be used. In other embodiments, $M_w$ can range from about 300,000 Daltons to about 1,000,000 Daltons, as described above, and PI can range from about 3 to about 6.

Using Base-Polymer-Unit-Derived Polymeric Compositions with Reduced Tg

While typically it is beneficial to decrease the drug release rate, sometimes the drug release rate is too low. At those times, it is desirable to increase drug release rate. The drug release rate is related to the polymer's drug permeability. Permeability is the product of the drug solubility and drug diffusivity in the polymer. Solubility is a thermodynamic property of the drug in the polymer. In turn, drug diffusivity is related to polymer structure. Typically, the polymer has a higher ultimate elongation when it has a lower $T_g$ and lower degree of crystallinity, if crystallinity is present. These same properties also lead to a higher drug diffusion rate through the polymer. Accordingly, in some invention embodiments, any or all layer(s) of the stent coating can be made of polymer compositions having reduced $T_g$. These compositions include a component derived from n-butyl methacrylate and a component derived from another acrylic compound. Such compositions can be of two types: first, the compositions comprising polymers that include units derived from a base-polymer-unit, and second, compositions that are physical blends of base polymer with at least one other acrylic polymer. Additionally, in some embodiments, any or all layer(s) of the stent coating can be made of polymer compositions having reduced $T_g$, the compositions including a component derived from base-polymer unit and a component derived from a non-acrylic compound.

Copolymers Including Units Derived From a Base-Polymer Unit

In some embodiments, the polymer composition can include a copolymer of a base-polymer unit with another acrylic monomer (base-polymer-unit copolymer (bpu copolymer)), where the $T_g$ of the bpu copolymer is lower than that of the $T_g$ of pure base polymer, which depends on molecular weight. The bpu copolymers can be of any kind, e.g., random, alternating, or block-copolymers. The $T_g$ of a bpu copolymer can be below about 20° C., for example, between about −30° C. to about 20° C., alternatively, from about 0° C. to about 20° C., for example, about 15° C.

Base-polymer-unit copolymers having reduced $T_g$ suitable for stent coatings can have an exemplary general formula (III-A), formula (III-B), formula (III-C), or formula (III-D):

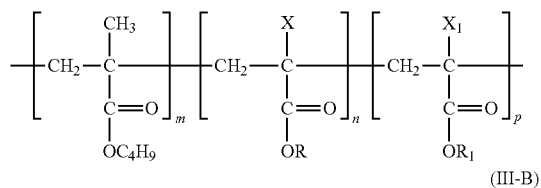

(III-A)

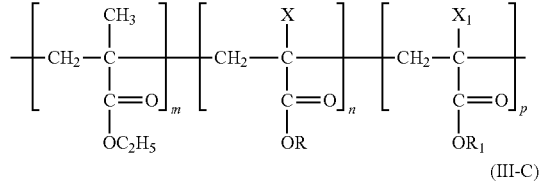

(III-B)

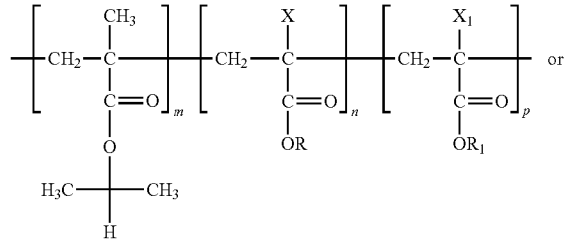

(III-C)

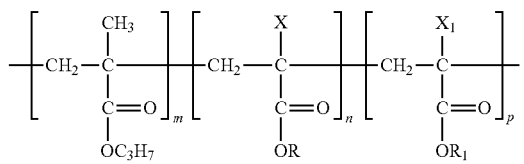

(III-D)

wherein:

X and $X_1$ is each, independently, a hydrogen atom or an alkyl group, such as methyl or ethyl group;

R and $R_1$ is each, independently, a $C_1$ to $C_{12}$ straight-chained or branched aliphatic radical; and m, n, and p are each integers, where m>0, n>0, and p≧0.

The total molecular weight ($M_w$) of a polymer according to formulas (III-A to III-D) can be from about 50,000 Daltons to about 500,000 Daltons, alternatively, from about 100,000 Daltons to about 400,000 Daltons, such as about 250,000 Daltons.

Examples of base-polymer-unit copolymers described by formulas (III-A to III-D) include poly(n-butyl methacrylate-co-n-hexyl methacrylate), poly(n-butyl methacrylate-co-2-ethylhexyl methacrylate), poly(n-butyl methacrylate-co-n-octyl methacrylate), poly(n-butyl methacrylate-co-2-ethoxyethyl methacrylate), poly(n-butyl methacrylate-co-2-methoxyethyl methacrylate), poly(n-butyl methacrylate-co-pentyl methacrylate), poly(n-butyl methacrylate-co-iso-decyl methacrylate), poly(n-butyl methacrylate-co-n-decyl methacrylate), poly(n-butyl methacrylate-co-n-dodecyl methacrylate), poly(n-butyl methacrylate-co-1-hexadecyl methacrylate), poly(n-butyl methacrylate-co-undecyl methacrylate) poly(n-butyl methacrylate-co-3,5,5-trimethylhexyl methacrylate and poly(n-butyl methacrylate-co-lauryl methacrylate). The exemplary formulas of some of these copolymers are shown below as formulas (IV), (V), and (VI), respectively. Those having ordinary skill in the art understand that the formulas (IV), (V), and (VI) are not the only formulas that illustrate the structure of the copolymers, and that the structures can take other forms.

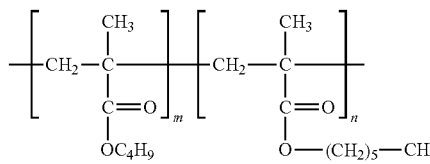

(IV)

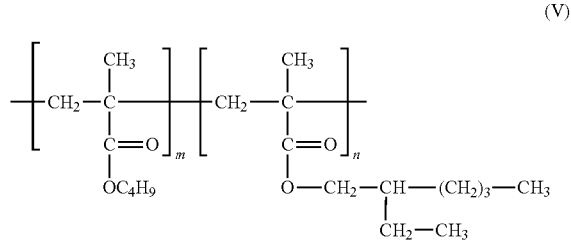

(V)

-continued

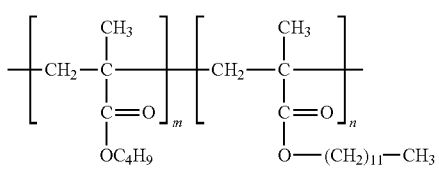

For a copolymer or a terpolymer, $T_g$ (on the Kelvin scale) is generally the mass-fraction-weighted average of the polymer constituents, according to the Fox equation. Consequently, a copolymer or terpolymer of formulas (III-A to III-D) can be designed with a predetermined $T_g$ value. For example, pure poly(lauryl methacrylate) has a $T_g$ of about 208 K (−65° C.), and poly(n-butyl methacrylate) has a $T_g$ of about 293 K (20° C.). Accordingly, poly(n-butyl methacrylate-co-lauryl methacrylate) (VI) [P(BMA-LMA)] having from about 2 mass % to about 25 mass % of lauryl methacrylate units, and the balance derived from n-butyl methacrylate can have a $T_g$ from about 17° C. to about −5° C., as shown in Table 1.

TABLE I

Glass Transition Temperature of Poly(n-butyl methacrylate-co-lauryl methacrylate)

| No. | Mass Content of Lauryl Methacrylate in the Copolymer, % | $T_g$ of the Copolymer, ° C. |
|---|---|---|
| 1 | 2 | 17 |
| 2 | 5 | 14 |
| 3 | 10 | 8 |
| 4 | 25 | −7 |

Physical Blends of Base Polymer with Other Acrylic Polymer(s)

In some embodiments, physical blends of base polymer with at least one other acrylic polymer where the $T_g$ of the blend is lower than the $T_g$ of pure base polymer can be used to make any or all layers of the stent coating. The $T_g$ of a blend can be below about 20° C., for example, from about −30° C. to about 20° C., more narrowly, between about −15° C. to about 18° C., for example, about 15° C.

Examples of acrylic polymers other than base polymer that can be combine with base polymer to form a blend include poly(n-hexyl methacrylate) (PHMA), poly(2-ethylhexyl methacrylate) (PEHMA), poly(n-octyl methacrylate), poly(2-ethoxyethyl methacrylate), poly(2-methoxyethyl methacrylate), poly(pentyl methacrylate), poly(iso-decyl methacrylate), poly(3,5,5-trimethylhexyl methacrylate), poly(n-decyl methacrylate), poly(n-dodecyl methacrylate), poly(1-hexadecyl methacrylate), poly(undecyl methacrylate), and poly(lauryl methacrylate) (PLMA).

As with copolymers, the $T_g$ of a blend of individual polymer (on the Kelvin scale) is generally the mass-fraction-weighted average of the polymers comprising the blend as long as the blend is non-crystalline the blend polymers are miscible. Accordingly, a physical blend of base polymer with at least one other acrylic polymer can have a predetermined value of $T_g$, in these examples 15° C. Examples of blends containing about 92 mass % of base polymer and 8 mass % of poly(decyl methacrylate), and blends containing about 69 mass % of base polymer and 21 mass % of poly(2-ethyl hexyl methacrylate) are useful. Polymer blends can include blends of base-polymer-unit copolymers with at least one acrylic polymer other than a base polymer or a base-polymer-unit copolymer, for example poly(n-hexyl methacrylate) (PHMA), poly(2-ethylhexyl methacrylate) (PEHMA), poly(n-octyl methacrylate), poly(2-ethoxyethyl methacrylate), poly(2-methoxyethyl methacrylate), poly(pentyl methacrylate), poly(iso-decyl methacrylate), poly(3,5,5-trimethylhexyl methacrylate), poly(n-decyl methacrylate), poly(n-dodecyl methacrylate), poly(1-hexadecyl methacrylate), poly(undecyl methacrylate), and poly(lauryl methacrylate) (PLMA).

Compositions Including a Non-Acrylic Component

According to other embodiments of the present invention, some non-acrylic monomers or polymers can be also used for making the stent coating. Some embodiments select non-acrylic monomers that polymerize by free radical or atom transfer process. Non-acrylic monomers are those that are substantially free of acrylic group (I) and of methacrylic group (II) shown above. Non-acrylic polymers are those that are derived from non-acrylic monomers. The term non-acrylic polymers includes non-acrylic homopolymers, copolymers, terpolymers, oligomers, and prepolymers.

In some embodiments, a copolymer of base-polymer-unit with a non-acrylic monomer(s) can be used in which the copolymer has a $T_g$ below about 20° C., for example, from about −30° C. to about 18° C., alternatively, from about −15° C. to about 18° C., for example, about 15° C. Examples of non-acrylic monomers that can be copolymerized with a base-polymer-unit to form such a copolymer include those shown in Table II. The copolymers of a base-polymer-unit with a non-acrylic monomer(s) that can be used can be of any kind, e.g., random, alternating, or block-copolymers. The copolymers of a base-polymer-unit with a non-acrylic monomer(s) can be designed by those having ordinary skill in the art so that the copolymers have a predetermined value of $T_g$, as described above for the a base-polymer-unit copolymers having the formula (III-A) to formula (III-D).

In some embodiments, physical blends of base polymer with at least one non-acrylic polymer can be used for any or all layers of the stent coating, where the $T_g$ of the blend is lower than that the $T_g$ of pure base polymer.

The $T_g$ of a blend can be below about 20° C., for example, from about −30° to about 20° C., more narrowly, from about −15° C. to about 18° C., for example, about 15° C.

TABLE II

Examples of non-acrylic polymers

| No. | Polymer | $T_g$, K |
|---|---|---|
| 1 | Poly(4-methoxycarbonyl-3-methyl-1-butenylene) | 326 |
| 2 | Poly(2-cyclohexylethylethylene) | 313 |
| 3 | Poly(hexadecylethylene) | 328 |
| 4 | Poly(iso-butylethylene) | 302 |
| 5 | Poly(iso-propylethylene), atactic | 323 |
| 6 | Poly(3,3-dimethylbutylethylene) | 326 |
| 7 | Poly(1,1,2-trimethylethylene) | 310 |
| 8 | Poly(4,4 dimethylpentylethylene) | 313 |
| 9 | Poly(propyl-2-propylene) | 300 |
| 10 | Poly(2,2,2-trifluoroethoxytrifluoroethylene) | 308 |
| 11 | Poly(4-methoxybenzoylethylene) | 319 |
| 12 | Poly(3,4-dimethoxybenzoylethylene) | 315 |
| 13 | Poly(vinyl fluoride) | 314 |
| 14 | Poly(vinyl acetate) | 305 |
| 15 | Poly(ethylene-co-vinyl alcohol)(EVAL) | 328 |
| 16 | Poly(cyclopentanoyloxyethylene) | 309 |
| 17 | Poly(formyloxyethylene), 60% syndiotactic | 310 |
| 18 | Poly(formyloxyethylene), 50% syndiotactic | 306 |

TABLE II-continued

Examples of non-acrylic polymers

| No. | Polymer | $T_g$, K |
|---|---|---|
| 19 | Poly(4-(sec-butoxymethyl) styrene) | 313 |
| 20 | Poly(4-butoxystyrene) | 320 |
| 21 | Poly(3-ethylstyrene) | 303 |
| 22 | Poly(n-octyl acrylamide) | 220 |
| 23 | Poly(4-butylstyrene) | 279 |
| 24 | Poly(4-octylstyrene) | 228 |
| 25 | Poly(butoxyethylene) | 218 |
| 26 | Poly(butylene adipate) | 223 |
| 27 | Poly(oxybutylene) | 185 |
| 28 | Poly(vinylidene fluoride) | 244 |

As in a of copolymers of a base-polymer-unit with non-acrylic monomers, for a blend of base polymer with individual non-acrylic polymers, the $T_g$ of the blend (on the Kelvin scale) is generally the mass-fraction-weighted average of the polymers comprising the blend as given by the Fox equation. Accordingly, a physical blend of base polymer with at least one other non-acrylic polymer can have a predetermined value of $T_g$, for example 15° C. Examples of blends that can be used include a blend containing about 29 mass % of base polymer and 71 mass % of poly(4-butylstyrene) and a blend containing about 82 mass % of base polymer and 18 mass % of poly(vinylidene fluoride).

At least one of the drug-polymer layer or the topcoat layer can include a base-polymer-unit- or PBMA-based polymer or blend having $T_g$ that falls within the previously described ranges. However, other polymers can also be used for the primer, drug-polymer, or top-coat layers so long as the polymer or a polymer blend forming either the drug-polymer layer or the topcoat layer have the $T_g$ within the specified ranges.

Representative examples of alternative polymers that can be used for making the primer, drug-polymer, or topcoat layers are shown below.

polyvinyl ethers
polyvinylidene halides polyvinyl aromatics
polyamides biomolecules poly(hydroxybutyrate-co-valerate)
polydioxanone
polyorthoester
polyanhydride
poly(glycolic acid)
poly(D,L-lactic acid)
poly(glycolic acid-co-trimethylene carbonate)
polyphosphoester
polyphosphoester urethane
poly(amino acids)
polycyanoacrylates
poly(trimethylene carbonate)
poly(iminocarbonate)
co-poly(ether-esters)
polyalkylene oxalates
polyphosphazenes
polyurethanes
silicones
polyesters
polyolefins
polyisobutylene polyvinyl methyl ether
polyvinylidene fluoride
polyvinylidene chloride
polystyrene
Nylon 66
polycaprolactam
fibrin
fibrinogen
cellulose
starch
collagen
hyaluronic acid ethylene-alphaolefin copolymers
polyvinyl chloride
poly(vinylidene fluoride-co-hexafluoropropene)
polyacrylonitrile
polyvinyl ketones
polyvinyl esters
acrylonitrile-styrene copolymers
ABS resins
ethylene-vinyl acetate copolymers
alkyd resins
polycarbonates
polyoxymethylenes
polyimides
polyethers
epoxy resins
polyurethanes
rayon
rayon-triacetate
cellulose
cellulose acetate
cellulose butyrate
cellulose acetate butyrate
cellophane
cellulose nitrate
cellulose propionate
cellulose ethers
carboxymethyl cellulose The coating of the present invention has been described in conjunction with a stent. However, the coating can also be used with a variety of other medical devices. Examples of implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The active agent, therapeutic substance or drug, the terms, which are used interchangeably, can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

Some embodiments of the present invention are further illustrated by the following examples.

Prophetic Example 1

A polymer solution containing from about 0.1 mass % to about 15 mass %, for example, about 2.0 mass % of EVAL and the balance, a solvent mixture of DMAC and ethanol, the solvent mixture containing about 80 mass % of DMAC to about 20 mass % of ethanol can be prepared. The solution can be applied onto a stent to form a primer layer. To apply the primer layer, a spray apparatus, such as an EFD 780S spray nozzle with a VALVEMATE 7040 control system (EFD, Inc. of East Providence, R.I.) can be used. The EFD 780S spray nozzle is an air-assisted external mixing atomizer. The composition is atomized by air and applied to the stent surfaces. During the process of applying the composition, the stent can optionally be rotated about its longitudinal axis, at a speed of about 50 to about 150 rpm. The stent can also be moved linearly along the same axis during the application.

The EVAL solution can be applied to a 13-mm TETRA stent (Guidant Corporation) in a series of 10-second passes, to deposit, for example, 10 μg of coating per spray pass. Instead of the 13-mm TETRA stent, another suitable stent can be used, for example, a 12-mm VISION stent (also Guidant Corporation). Between the spray passes, the stent can be dried for about 10 seconds using flowing air with a temperature of about 60° C. Five spray passes can be applied, followed by baking the primer layer at about 110° C. for about 1-hour. As a result, a primer layer can be formed having a solids content of about 50 μg. "Solids" means the amount of the dry residue deposited on the stent after all volatile organic compounds (e.g., the solvent) have been removed.

A drug-containing formulation can be prepared comprising:
(a) from about 0.1 mass % to about 15 mass %, for example, about 2.0 mass % of EVAL;
(b) from about 0.1 mass % to about 2 mass %, for example, about 1.0 mass % of an active agent, for example, EVEROLIMUS; and
(c) the balance, a solvent mixture of DMAC and pentane, the solvent mixture containing about 80 mass % of DMAC and about 20 mass % of pentane.

In a manner identical to the application of the primer layer, five spray passes can be performed, followed by baking the drug-polymer layer at about 50° C. for about 2 hours, to form the drug-polymer layer having a solids content from about 30 μg and 750 μg, for example, about 90 μg, and a drug content of from about 10 μg to about 250 μg, for example, 30 μg.

Finally, a topcoat composition can be prepared, comprising:
(a) from about 1 mass % to about 10 mass %, for example, about 2 mass % of poly(n-butyl methacrylate) (PBMA) having weight average molecular weight of about 500,000; and
(b) the balance, a solvent mixture of acetone and cyclohexanone, the solvent mixture containing about 70 mass % of acetone and about 30 mass % of cyclohexanone.

In a manner identical to the application of the primer layer and the drug-polymer layer, a number of spray passes are performed followed by final baking at about 50° C. for about 1 hour. As a result, the topcoat membrane can be formed with a solids content of from about 40 μg to about 150 μg, for example, about 60 μg.

Prophetic Example 2

A stent can be coated as described in Prophetic Example 1, where PBMA in the topcoat can have a polydispersity index of about 4. The weight average molecular weight of PBMA can be from about 150,000 Daltons to about 400,000 Daltons.

Prophetic Example 3

A stent can be coated as described in Prophetic Example 1, except that in the topcoat layer PBMA can be replaced by the same amount of poly(n-butyl methacrylate-co-lauryl methacrylate) [P(BMA-LMA)] having from about 2 mass % to about 25 mass %, for example, about 10 mass % of units derived from lauryl methacrylate, and the balance of units derived from n-butyl methacrylate. The solvent that can be used for dissolving Poly(BMA-LMA) prior to forming the topcoat layer can be a solvent mixture of acetone and cyclohexanone, the solvent mixture containing about 70 mass % of acetone and about 30 mass % of cyclohexanone.

Prophetic Example 4

A stent can be coated with a primer layer and a drug-polymer layer as described in Prophetic Example 1. A topcoat composition can be prepared, comprising:

(a) from about 1 mass % to about 10 mass %, for example, about 1.8 mass % PBMA;
(b) from about 0.1 mass % to about 10 mass %, for example, about 0.2 mass % poly(lauryl methacrylate) (PLMA); and
(c) the balance, a solvent mixture of acetone and xylene, the solvent mixture containing about 50 mass % of acetone and about 50 mass % of xylene.

In a manner like the application of the primer layer and the drug-polymer layer, a number of spray passes are performed followed by final baking at about 60° C. for about 1 hour. As a result, the topcoat membrane can be formed, the membrane having a solids content of from about 40 µg to about 120 µg, for example, about 75 µg.

Prophetic Example 5

A polymer solution containing from about 0.1 mass % to about 15 mass %, for example, about 2.0 mass % of PBMA and, the balance, a solvent mixture of acetone and cyclohexanone containing about 70 mass % of acetone to about 30 mass % of cyclohexanone can be prepared. The solution can be applied onto a stent to form a primer layer. To apply the primer layer, a spray apparatus, such as an EFD 780S spray nozzle with a VALVEMATE 7040 control system (EFD, Inc. of East Providence, R.I.) can be used. The EFD 780S spray nozzle is an air-assisted external mixing atomizer. The composition is atomized by air and applied to the stent surfaces. While applying the composition, the stent can optionally be rotated about its longitudinal axis, at a speed of about 50 to about 150 rpm. The stent can also be linearly moved along the same axis during the application.

The PBMA solution can be applied to a 12-mm small VISION stent (Guidant Corporation) in a series of 10-second passes, to deposit, for example, 10 µg of coating per spray pass. Between the spray passes, the stent can be dried for about 10 seconds using flowing air with a temperature of about 60° C. Five spray passes can be applied, followed by baking the primer layer at about 80° C. for about 1 hour. As a result, a primer layer can be formed having a solids content of about 50 µg. "Solids" means the amount of the dry residue deposited on the stent after all volatile organic compounds (e.g., the solvent) have been removed.

A drug-containing formulation can be prepared comprising:
(a) from about 0.1 mass % to about 15 mass %, for example, about 2.0 mass % of poly(n-butyl methacrylate-co-4-butylstyrene) wherein 66% of the mass is derived from BMA units and 34% of the mass is derived from 4-butylstyrene units;
(b) from about 0.1 mass % to about 2 mass %, for example, about 0.8 mass % of an active agent, for example, SIROLIMUS; and
(c) the balance, a solvent mixture of acetone and 4-methyl-2-pentanone, the solvent mixture containing about 50 mass % of acetone and about 50 mass % of 4-methyl-2-pentanone.

In a manner identical to the application of the primer layer, nineteen spray passes can be performed, followed by baking the drug-polymer layer at about 50° C. for about 2 hours, to form the drug-polymer reservoir layer having a solids content from about 30 µg and 750 µg, for example, about 190 µg, and a drug content of from about 10 µg to about 250 µg, for example, 50 µg.

Prophetic Example 6

A stent can be coated with a primer layer as described in Prophetic Example 5. A drug reservoir composition can be prepared comprising:

(a) from about 1 mass % to about 10 mass %, for example, about 1.8 mass % PBMA;
(b) from about 0.1 mass % to about 10 mass %, for example, about 0.2 mass % poly(butylene adipate); and
(c) from about 0.1 mass % to about 2 mass %, for example, about 0.5 mass % of an active agent, for example, PACLITAXEL
(c) the balance, a solvent mixture of acetone and xylene, the solvent mixture containing about 50 mass % of acetone and about 50 mass % of xylene.

In a manner identical to the application of the primer layer, a number of spray passes are performed followed by final baking at about 60° C. for about 1 hour. As a result, a drug reservoir layer can be formed having a solids content of about 40 µg to about 200 µg, for example, about 125 µg.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists in that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

What is claimed is:

1. A medical article comprising an implantable medical device comprising a base-polymer-unit-derived polymer with a degree of an elongation at failure from about 20% to about 500% wherein the base-polymer-unit-derived polymer is poly(n-butyl methacrylate-co-lauryl methacrylate).

2. The medical article of claim 1 wherein the implantable medical device is a stent.

3. The medical article of claim 1 wherein the base polymer has a weight average molecular weight of about 200,000 Daltons to about 1,000,000 Daltons.

4. The medical article of claim 1 wherein the base polymer has a polydispersity index of about 3 to about 6.

5. The medical article of claim 1 wherein the base-polymer-unit-derived polymer has a glass transition temperature below about 20° C.

6. The medical article of claim 5 wherein the glass transition temperature is about −30° C. to about 20° C.

7. The medical article of claim 1 wherein the medical device further comprises one or any combination of vascular-smooth-muscle-cell-activity inhibitors, antiproliferatives, antineoplastics, antimitotics, anti-inflammatories, antiplatelets, anticoagulants, antifibrins, antithrombins, antibiotics, antiallergics and antioxidants.

8. The medical article of claim 5 wherein the medical device further comprises one or any combination of vascular-smooth-muscle-cell-activity inhibitors, antiproliferatives, antineoplastics, antimitotics, anti-inflammatories, antiplatelets, anticoagulants, antifibrins, antithrombins, antibiotics, antiallergics and antioxidants.

9. A method comprising depositing a coating on an implantable medical device wherein the coating comprises a base-polymer-unit-derived polymer with a degree of an elongation at failure of about 20% to about 500%, wherein the base-polymer-unit-derived polymer is poly(n-butyl methacrylate-co-lauryl methacrylate).

10. The method of claim 9 wherein the implantable medical device is a stent.

11. The method of claim 9 wherein the base polymer has a weight average molecular weight of about 200,000 Daltons to about 1,000,000 Daltons.

12. The method of claim 11 wherein the base polymer has a polydispersity index of about 3 to about 6.

13. The method of claim 9 wherein the base polymer has a polydispersity index of about 3 to about 6.

14. The method of claim 9 wherein the copolymer has a glass transition temperature below about 20° C.

15. The method of claim 14 wherein the glass transition temperature of about −30° C. to about 20° C.

16. The method of claim 9 wherein the medical device further comprises one or any combination of vascular-smooth-muscle-cell-activity inhibitors, antiproliferatives, antineoplastics, antimitotics, anti-inflammatories, antiplatelets, anticoagulants, antifibrins, antithrombins, antibiotics, antiallergics and antioxidants.

17. The method of claim 15 wherein the medical device further comprises one or any combination of vascular-smooth-muscle-cell-activity inhibitors, antiproliferatives, antineoplastics, antimitotics, anti-inflammatories, antiplatelets, anticoagulants, antifibrins, antithrombins, antibiotics, antiallergics and antioxidants.

* * * * *